United States Patent

Hoff et al.

[11] Patent Number: 4,537,898
[45] Date of Patent: Aug. 27, 1985

[54] LIQUID FORMULATIONS OF DIHYDROPYRIDINES

[75] Inventors: Dieter Hoff, Leverkusen; Klaus-Dieter Rämsch, Wuppertal, both of Fed. Rep. of Germany

[73] Assignee: Bayer Aktiengesellschaft, Leverkusen, Fed. Rep. of Germany

[21] Appl. No.: 579,833

[22] Filed: Feb. 13, 1984

[30] Foreign Application Priority Data

Mar. 3, 1983 [DE] Fed. Rep. of Germany ....... 3307422

[51] Int. Cl.$^3$ .................................. A61K 31/455
[52] U.S. Cl. .................................. 514/356; 514/941
[58] Field of Search .................................. 424/266

[56] References Cited

U.S. PATENT DOCUMENTS 3,784,684 8/1972 Bossert et al. ........................ 424/37

FOREIGN PATENT DOCUMENTS

| 0001247 | 4/1979 | European Pat. Off. | 424/266 |
| 0007293 | 1/1980 | European Pat. Off. | 424/266 |
| 56-115726 | 2/1980 | Japan | 424/266 |
| 57-167911 | 4/1981 | Japan | 424/266 |
| 1173862 | 12/1969 | United Kingdom | 424/266 |
| 1456618 | 11/1976 | United Kingdom | 424/266 |

OTHER PUBLICATIONS

Remington's Pharmaceutical Sciences, Mack Publishing Company, (Easton, Pa.), pp. 290–292, (1980).

Primary Examiner—Elbert L. Roberts
Assistant Examiner—Joyce L. Morrison
Attorney, Agent, or Firm—Sprung Horn Kramer & Woods

[57] ABSTRACT

A rapidly absorbable liquid formulation of a dihydropyridine comprising, by weight, about 0.5 to 10 parts of a dihydropyridine of the formula

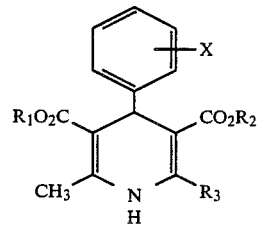

in which $R_1$ is $C_1$–$C_4$-alkyl, optionally substituted by $C_2$–$C_3$-alkoxy, $R_2$ is $C_1$–$C_{10}$-alkyl, optionally substituted by $C_1$–$C_3$-alkoxy, trifluoromethyl or N-methyl-N-benzylamino, $R_3$ is $C_1$–$C_4$-alkyl, cyano or hydroxymethyl, and X is 2- or 3-nitro, 2,3-dichloro or 2,3=N—O—N=, 20 to 60 parts of a solubilizing agent and 80 to 40 parts of a diluent.

5 Claims, 1 Drawing Figure

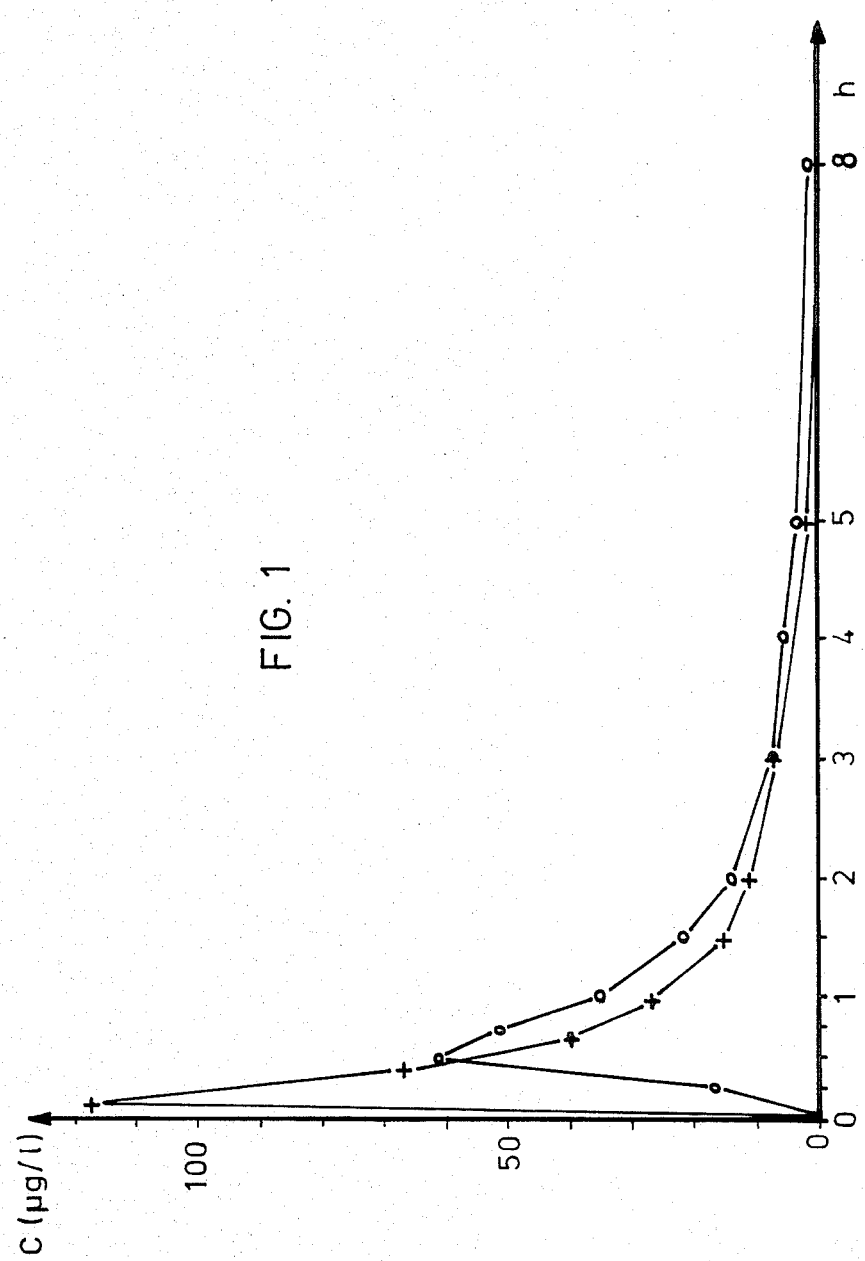

LIQUID FORMULATIONS OF DIHYDROPYRIDINES

The invention relates to liquid formulations of dihydropyridines, in particular drop formulations, a process for their preparation, and their use in combating diseases.

It is known that dihydropyridines have very powerful actions which influence the circulation (compare British Pat. No. 1,173,862). Because they are sensitive to light and sparingly soluble, a number of difficulties arise during galenical formulation of drug specialities, which can be seen from the numerous patents and patent applications for particular formulations of this active compound. Thus, for example, U.S. Pat. No. 3,784,684 relates to particular gelatine biteable capsules containing nifedipine, by means of which the coronary action of nifedipine can advantageously be utilized. British Pat. No. 1,456,618 moreover describes solid medicament formulations which likewise ensure good bioavailability of nifedipine. Solid medicament forms in which the sparingly soluble characteristics of nifedipine are said to be compensated by using certain solubilizing agents and surface-active substances are also described in DE-OS (German Published Specification) No. 2,822,882. In European Offenlegungsschrift (European Published Specification) No. 1,247, the absorbency of nifedipine is also said to be improved by using polyethylene glycol and certain porous carrier substances.

All the attempts which have hitherto been made to compensate the poor solubility of nifedipine by certain measures and at the same time to ensure good bioavailability have a number of disadvantages. The use of surface-active substances, solubilizing agents and certain carrier substances which have a particular surface, for example are porous, frequently leads to administration forms in which the products are undesirably large. To facilitate swallowing, such tablets or capsules are frequently converted into specific shapes, such as, for example, ellipsoids or longitudinal shapes, but this still no longer gives satisfactory results for products weighing more than 400 mg. More frequent intake of smaller products is also not a satisfactory solution.

A tablet containing nifedipine which is characterized in that the crystalline active compound has a certain specific surface area is also known (DE-OS (German Published Specification) No. 3,033,919). Following oral administration of the tablet, the plasma concentration rises and remains at a high value for many hours.

There is still a need to provide a formulation for dihydropyridines which has a very rapid absorption of active compound. When the active compound is administered as a tablet, the plasma concentration rises only slowly, because the compound is sparingly soluble. Accordingly, a more rapid onset of action cannot be achieved.

Administration of the active compound in capsule form, in the core of which the active compound is dissolved, leads to a more rapid build-up of the plasma concentration in comparison with the tablet administration form, but in many cases an even more rapid onset of action is desirable.

Moreover, there is a need in medicine also to provide drop formulations, since in particular older patients can be motivated more easily to take drops than capsules or tablets.

Furthermore, drop formulations can also be administered to unconscious patients without complications. The active compound can likewise be fed to the body by infusion.

As already mentioned above, all dihydropyridines are sparingly soluble in an aqueous medium. For example, the solubility of nimodipine in water is 0.2 mg per 100 ml.

It has now been found that when certain solubilizing agents are added to the drop solution in a concentration of 20%–60%, based on the total amount of solution, the very sparingly soluble active compound readily dissolves and also remains in solution. It has furthermore been found that when the drop solution according to the invention is diluted with aqueous media, such a dilution remains stable and clear over a relatively long period, depending on the degree of dilution.

The invention thus relates to liquid formulations of dihydropyridines of the formula I

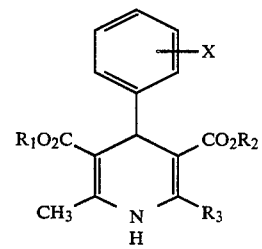

in which
$R_1$ denotes $C_1$–$C_4$-alkyl, optionally substituted by $C_1$–$C_3$-alkoxy,
$R_2$ denotes $C_1$–$C_{10}$-alkyl, optionally substituted by $C_1$–$C_3$-alkoxy, trifluoromethyl or N-methyl-N-benzylamino,
$R_3$ denotes $C_1$–$C_4$-alkyl, cyano or hydroxymethyl and
X denotes 2- or 3-nitro, 2,3-dichloro or a 2,3-ring member consisting of =N—O—N=,
which are characterized in that the dihydropyridines are dissolved in amounts of 0.5–10% by weight, preferably 1–5% by weight, based on 100 parts by weight of a solution consisting of 20 to 60% by weight, preferably 30–50% by weight, of a solubilizing agent and 80 to 40% by weight, preferably 70–50% by weight, of a diluent.

The compounds in the table which follows may be mentioned as preferred dihydropyridines:

TABLE

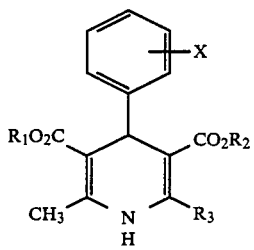

| No. | X | $R^1$ | $R^2$ | $R^3$ | Generic |
|---|---|---|---|---|---|
| 1 | 2-$NO_2$ | $CH_3$ | $CH_3$ | $CH_3$ | Nifedipine |
| 2 | 3-$NO_2$ | $nPrOCH_2CH_2$ | $nPrOCH_2CH_2$ | $CH_3$ | Niludipine |
| 3 | 3-$NO_2$ | $C_2H_5$ | $CH_3$ | $CH_3$ | Nitrendipine |
| 4 | 2-$NO_2$ | $CH_3$ | $(CH_3)_2CHCH_2$ | $CH_3$ | Nisoldipine |
| 5 | 3-$NO_2$ | $CH(CH_3)_2$ | $(CH_2)_2-O-CH_3$ | $CH_3$ | Nimodipine |
| 6 | 3-$NO_2$ | $C_2H_5$ | $C_{10}H_{21}(n)$ | $CH_3$ | |
| 7 | 2-Cl | $CH_3$ | $CH_2-CF_3$ | $CH_3$ | |
| 8 | 2-Cl | $C_2H_5$ | $CH_2-CF_3$ | $CH_3$ | |
| 9 | 3-$NO_2$ | $CH(CH_3)_2$ | $n\text{-}PrO-CH_2CH_2$ | $CH_3$ | |
| 10 | 3-$NO_2$ | $CH_3$ | $C_6H_5CH_2N(CH_3)CH_2CH_2$ | $CH_3$ | Nicardipine |
| 11 | 2,3-$Cl_2$ | $C_2H_5$ | $CH_3$ | $CH_3$ | Felodipine |
| 12 | 2,3=N—O—N= | $C_2H_5$ | $C_2H_5$ | $CH_3$ | |
| 13 | 2,3=N—O—N= | $CH_3$ | $CH(CH_3)_2$ | $CH_3$ | |
| 14 | 3-$NO_2$ | $C_2H_5$ | $C_2H_5$ | $CH_2OH$ | |
| 15 | 3-$NO_2$ | $CH_3$ | $CH_3$ | CN | | n-Pr = n-propyl

Compounds Nos. 1, 3, 4, 5 and 7 may be mentioned as preferred.

Solubilizing agents is understood as meaning substances which solubilize active compounds which are insufficiently soluble in an aqueous medium, usually with the formation of micelles. Non-ionic surface-active agents are used for this. The following compounds are suitable solubilizing agents for the drop solutions according to the invention: sorbitan monolaurate, sorbitan monopalmitate, sorbitan monostearate, sorbitan monooleate and sorbitan sesquioleate; polyethylene glycol (20)-sorbitan monolaurate, polyethylene glycol (4)-sorbitan monolaurate, polyethylene glycol (20)-sorbitan monopalmitate, polyethylene glycol (20)-sorbitan tristearate, polyethylene glycol (20)-sorbitan monooleate and polyethylene glycol (20)-sorbitan trioleate, but especially glycerol polyethylene glycol oxystearate oxyethylated with about 35 mols of ethylene oxide, glycerol polyethylene glycol oxystearate oxyethylated with about 45 mols of ethylene oxide and glycerol polyethylene glycol oxystearate oxyethylated with about 60 mols of ethylene oxide.

Diluents which can be used in combination with the solubilizing agents are water and all the solvents which are miscible with water or the solubilizing agents and are suitable for oral purposes. Examples of suitable solvents are: ethanol, glycerol, 1,2-propylene glycol, polyethylene glycol 200, polyethylene glycol 400 and polyethylene glycol 600.

The drops can also be aromatized. Examples of suitable aromas are: peppermint oil, contramarum aroma, cinnamon aroma, boonekamp aroma, orange aroma or lemon aroma.

Sweeteners, such as, for example, saccharin or the sodium salt of saccharin, can also be added.

Since the dihydropyridine derivatives are very sensitive to light, it may prove to be necessary for certain dyestuffs to be added to the drop solutions to protect them from light and for the purpose of stabilization. Suitable dyestuffs can be, for example, apocarotenal, canthaxanthine, tartrazine (E 102), amaranth (E 123) and erythrosine (E 127), but in particular Yellow Orange S (E 110). The concentration of the particular dyestuff is 0.01–0.5% by weight, preferably 0.1–0.4% by weight, based on the liquid formulation.

The liquid formulations can be prepared by warming the solubilizing agents, for example to temperatures of 30° to 70° C., dissolving the dihydropyridine therein, for example with stirring, adding the diluent and, if appropriate, adding the remaining constituents.

EXAMPLE 1

| | |
|---|---|
| Nimodipine | 40.000 g |
| Glycerol polyethylene glycol oxystearate oxyethylated with about 45 mols of ethylene oxide | 400.000 g |
| Ethanol | 500.600 g |

EXAMPLE 2

| | |
|---|---|
| Nimodipine | 40.000 g |
| Glycerol polyethylene glycol oxystearate oxyethylated with about 45 mols of ethylene oxide | 400.000 g |
| Contramarum aroma | 0.750 g |
| Ethanol | 500.600 g |

EXAMPLE 3

| | |
|---|---|
| Nimodipine | 40.000 g |
| Glycerol polyethylene glycol oxystearate oxyethylated with about 35 mols of ethylene oxide | 435.000 g |
| Demineralized water | 50.000 g |
| The sodium salt of saccharin | 9.000 g |
| Cinnamon aroma | 0.500 g |
| Ethanol | 529.200 g |

EXAMPLE 4

| | |
|---|---|
| Nisoldipine | 20.000 g |
| Glycerol polyethylene glycol oxystearate oxyethylated with about 60 mols of ethylene oxide | 300.000 g |
| Demineralized water | 100.000 g |
| Ethanol | 533.700 g |

EXAMPLE 5

| | |
|---|---|
| Nisoldipine | 25.000 g |
| Polyethylene glycol (20)-sorbitan monolaurate | 360.000 g |
| Saccharin | 5.000 g |
| Ethanol | 700.000 g |

EXAMPLE 6

| | |
|---|---|
| Nifedipine | 40.000 g |
| Glycerol polyethylene glycol oxystearate oxyethylated with about 45 mols of ethylene oxide | 450.000 g |
| Polyethylene glycol 400 | 80.000 g |
| Demineralized water | 80.000 g |
| Boonekamp aroma | 0.800 g |
| Ethanol | 530.600 g |

EXAMPLE 7

| | |
|---|---|
| Nifedipine | 40.000 g |
| Glycerol polyethylene glycol oxystearate oxyethylated with about 45 mols of ethylene oxide | 420.000 g |
| Orange aroma | 20.000 g |
| Saccharin | 9.000 g |
| Ethanol | 600.200 g |

EXAMPLE 8

| | |
|---|---|
| Nimodipine | 20.000 g |
| Polyethylene glycol (20)-sorbitan monolaurate | 380.000 g |
| Polyethylene glycol 400 | 80.000 g |
| Ethanol | 607.300 g |

EXAMPLE 9

| | |
|---|---|
| 3-Methyl 5-trifluoroethyl diester of 4-(2-chlorophenyl)-2,6-dimethyl-1,4-dihydropyridine-3,5-dicarboxylic acid | 30.000 g |
| Glycerol polyethylene glycol oxystearate oxyethylated with about 35 mols of ethylene oxide | 400.000 g |
| Lemon aroma | 10.000 g |
| Ethanol | 619.600 g |

EXAMPLE 10

| | |
|---|---|
| 3-methyl 5-trifluoromethyl diester of 4-(2-chlorophenyl)-2,6-dimethyl-1,4-dihydropyridine-3,5-dicarboxylic acid | 40.000 g |
| Polyethylene glycol (20)-sorbitan monopalmitate | 500.000 g |
| 1,2-Propylene glycol | 200.000 g |
| Peppermint oil | 1.000 g |
| Ethanol | 518.000 g |

EXAMPLE 11

| | |
|---|---|
| Nifedipine | 20.000 g |
| Glycerol polyethylene glycol oxystearate oxyethylated with about 45 mols of ethylene oxide | 400.000 g |
| Orange aroma | 20.000 g |
| Yellow Orange S | 4.000 g |
| Demineralized water | 100.000 g |
| Ethanol | 509.700 g |

EXAMPLE 12

| | |
|---|---|
| Nisoldipine | 20.000 g |
| Glycerol polyethylene glycol oxystearate oxyethylated with about 45 mols of ethylene oxide | 420.000 g |
| Yellow Orange S | 4.000 g |
| Demineralized water | 110.000 g |
| Ethanol | 513.300 g |

Because of its properties, the liquid formulation is suitable for the prophylaxis of acute and chronic ischaemic heart disease in the broadest sense, for the therapy of high blood pressure and for the treatment of disorders in cerebral and peripheral blood flow.

In general, it has proved advantageous, in the case of intravenous administration, to administer amounts of about 0.001 to 10 mg/kg of body weight, preferably about 0.05 to 5 mg/kg of body weight, of dihydropyridine per day to achieve effective results, and in the case of oral administration the dosage is about 0.05 to 20 mg/kg of body weight, preferably 0.5 to 5 mg/kg of body weight, per day.

Nevertheless, it may at times be necessary to deviate from the amounts mentioned, and in particular to do so as a function of the body weight or the type of administration route, but also because of the animal species and its individual behaviour towards the medicament or the time or interval at which administration takes place. Thus, in some cases it may be sufficient to manage with less than the abovementioned minimum amount, while in other cases the upper limit mentioned must be exceeded. Where relatively large amounts are administered, it may be advisable to divide these into several individual administrations throughout the day. The same dosage range is envisaged for administration in human medicine. The above statements also apply in the general sense.

Administration of a drop solution gives a more rapid absorption of active compound and surprisingly higher blood level values in comparison with a capsule. Such drop formulations can also be easily administered by stomach tube, without complications, to unconscious patients suffering from a vasospasm following subarachnoidal haemorrhage.

The more rapid absorption of active compound and the higher blood level value may be illustrated by the example of nimodipine with the aid of the following experiments, taken in conjunction with the accompanying drawing wherein:

The FIGURE shows the content of active ingredient in the bloodstream after administration of a liquid formulation in accordance with the invention (− + −) and of a capsule in accordance with the prior art.

Six volunteer test subjects each take 60 mg of nimodipine orally with 200 ml of water. After certain periods of time after taking the active compound, the blood level values are determined by gas liquid chromatography.

After the formulation, according to the invention, in Example 1 has been taken, the highest blood plasma concentration is 115.5±78.3 µg/liter after 15 minutes. After 24 hours, the corresponding value is below the detection limit of 2 g/liter. The mean area under curve 1 (AUC) is 107.6±51.4 hours µg/liter. The mean value for the bioavailability is calculated as 8.6±4.6%.

The nimodipine capsule taken for comparison gives, as a value for the highest blood plasma concentration, 60.8±48.0 µg/liter after 30 minutes. After 24 hours, the corresponding value is again below the detection limit. The mean value of the bioavailability is calculated as 8.8±4.4%. The mean area under curve 1 (AUC) is 91.6±35.8 hours µg/liter.

The difference in action between the liquid formulation according to the invention and the corresponding capsule can easily be seen from the curve and from the tabular values. After 15 minutes, the blood concentration is 16.6±12.4 µg/liter when the capsule is taken, whereas the corresponding value for the liquid formulation is 115.5±78.3 µg/liter.

It will be understood that the specification, examples and drawing are illustrative but not limitative of the present invention and that other embodiments within the spirit and scope of the invention will suggest themselves to those skilled in the art.

What is claimed is:

1. A liquid formulation of a dihydropyridine comprising, by weight, about 1 to 5 parts of a dihydropyridine selected from the group consisting of nisoldipine, nimodipine and 3-methyl 5-trifluoroethyl diester of 4-(2-chlorophenyl)-2,6-dimethyl-1,4-dihydropyridine-3,5-dicarboxylic acid, 30 to 50 parts of weight of a solubilizing agent comprising glycerol polyethylene glycol oxystearate oxyethylated with about 35, 45 or 60 mols of ethylene oxide and 70 to 50 parts of a diluent consisting essentially of water, ethanol, glycerol, 1,2-propylene glycol, polyethylene glycol 200, polyethylene glycol 400 or polyethylene glycol 600.

2. A liquid formulation according to claim 1, wherein the dihydropyridine comprises nisoldipine.

3. A liquid formulation according to claim 1, wherein the dihydropyridine comprises nimodipine.

4. A liquid formulation according to claim 1, wherein the dihydropyridine comprises the 3-methyl 5-trifluoroethyl diester of 4-(2-chlorophenyl)-2,6-dimethyl-1,4-dihydropyridine-3,5-dicarboxylic acid.

5. A liquid formulation according to claim 1, in which the dihydropyridine is nimodipine, the solubilizing agent is glycerol polyethylene glycol oxystearate oxyethylated with about 45 mols of ethylene oxide and the diluent comprises ethanol.

* * * * *

TABLE 1

Blood concentration in 6 test subjects following oral intake of a liquid formulation containing 60 mg of nimodipine

| | time after intake (hours) | | | | | | | | | | $AUC_{O\text{-}inf.}$ (hours µg/l) | Bioavailability % |
|---|---|---|---|---|---|---|---|---|---|---|---|---|
| | 0.25 | 0.5 | 0.75 | 1.0 | 1.5 | 2.0 | 3.0 | 5.0 | 8.0 | 24.0 | | |
| 1 | 20 | 36 | 22 | 14 | 10 | 7 | 2 | <2 | <2 | <2 | 37.6 | 3.6 |
| 2 | 244 | 106 | 57 | 37 | 18 | 12 | 7 | <2 | <2 | <2 | 150.1 | 8.6 |
| 3 | 157 | 66 | 43 | 29 | 14 | 11 | 9 | <2 | <2 | <2 | 142.0 | 16.1 |
| 4 | 75 | 28 | 20 | 13 | 10 | 7 | 5 | <2 | <2 | <2 | 63.2 | 6.4 |
| 5 | 93 | 107 | 59 | 46 | 24 | 19 | 11 | 7 | <2 | <2 | 162.7 | 8.5 |
| 6 | 80 | 55 | 36 | 22 | 17 | 11 | 9 | 3 | <2 | <2 | 89.7 | — |
| x̄ | 115.5 | 66.3 | 39.5 | 26.8 | 15.5 | 11.2 | 7.2 | 2.3 | <2 | <2 | 107.6 | 8.6 |
| ±s.d. | 78.3 | 33.9 | 16.7 | 13.1 | 5.4 | 4.4 | 3.3 | 2.4 | — | — | 51.4 | 4.6 |

TABLE 2

Blood concentration in 6 test subjects following oral intake of a capsule containing 60 mg of nimodipine (comparison)

| | time after intake (hours) | | | | | | | | | | | $AUC_{O\text{-}inf.}$ (hours µg/l) | Bioavailability % |
|---|---|---|---|---|---|---|---|---|---|---|---|---|---|
| | 0.25 | 0.5 | 0.75 | 1.0 | 1.5 | 2.0 | 3.0 | 4.0 | 5.0 | 8.0 | 24.0 | | |
| | 2 | 27 | 48 | 29 | 27 | 13 | 9 | 5 | 3 | 3 | 2 | 113.0 | 7.5 |
| | 25 | 25 | 83 | 53 | 22 | 14 | — | 4 | <2 | <2 | <2 | 89.2 | 12.7 |
| | 35 | 134 | 36 | 19 | 10 | 8 | 3 | 2 | <2 | <2 | <2 | 76.5 | 8.6 |
| | 19 | 41 | 31 | 22 | 19 | 10 | 4 | 2 | <2 | <2 | <2 | 54.9 | 5.5 |
| | 12 | 109 | 78 | 60 | 34 | 24 | 11 | 7 | 6 | 3 | <2 | 151.8 | 15.0 |
| | 6 | 29 | 34 | 26 | 19 | 12 | 6 | 9 | 3 | — | <2 | 64.2 | 3.3 |
| x̄ | 16.6 | 60.8 | 51.5 | 34.6 | 21.6 | 13.3 | 6.7 | 4.7 | 2.5 | 1.1 | <2 | 91.6 | 8.8 |
| ±s.d. | 12.4 | 48.0 | 23.1 | 17.4 | 7.9 | 5.6 | 3.5 | 2.6 | 2.1 | 1.3 | — | 35.8 | 4.4 |